(12) United States Patent
Kang et al.

(10) Patent No.: US 11,639,891 B2
(45) Date of Patent: May 2, 2023

(54) INTEGRATED PHOTOACOUSTIC GAS SENSOR AND METHOD FOR MANUFACTURING THE SAME

(71) Applicant: KOREA INSTITUTE OF SCIENCE AND TECHNOLOGY, Seoul (KR)

(72) Inventors: Joonhyun Kang, Seoul (KR); Il Ki Han, Seoul (KR); S. Joon Kwon, Seoul (KR); Young Min Jhon, Seoul (KR)

(73) Assignee: KOREA INSTITUTE OF SCIENCE AND TECHNOLOGY, Seoul (KR)

( * ) Notice: Subject to any disclaimer, the term of this patent is extended or adjusted under 35 U.S.C. 154(b) by 0 days.

(21) Appl. No.: 17/498,755

(22) Filed: Oct. 12, 2021

(65) Prior Publication Data
US 2022/0120669 A1    Apr. 21, 2022

(30) Foreign Application Priority Data
Oct. 20, 2020  (KR) .................. 10-2020-0135896

(51) Int. Cl.
*G01N 21/17* (2006.01)
*G01N 33/00* (2006.01)

(52) U.S. Cl.
CPC ..... *G01N 21/1702* (2013.01); *G01N 33/0027* (2013.01); *G01N 2021/1704* (2013.01); *G01N 2201/06113* (2013.01)

(58) Field of Classification Search
CPC .......... G01N 21/1702; G01N 33/0027; G01N 2021/1704; G01N 2021/1708; G01N 2201/06113; G01N 29/2418
See application file for complete search history.

(56) References Cited

U.S. PATENT DOCUMENTS

| 8,359,904 B2 | 1/2013 | Nicoletti et al. |
| 8,857,242 B2 | 10/2014 | Heidrich et al. |
| 2009/0128819 A1 | 5/2009 | Van Kesteren et al. |
| 2011/0088453 A1* | 4/2011 | Nicoletti ............ G01N 21/1702 73/24.02 |

(Continued)

FOREIGN PATENT DOCUMENTS

| EP | 2019307 A1 | 1/2009 |
| JP | 4231854 B2 | 3/2009 |

(Continued)

OTHER PUBLICATIONS

P. Patimisco et al., "Quartz-Enhanced Photoacoustic Spectroscopy: A Review," Sensors, Mar. 2014, pp. 6165-6206, vol. 14.

(Continued)

*Primary Examiner* — Suman K Nath
(74) *Attorney, Agent, or Firm* — Cantor Colburn LLP (57) ABSTRACT

The present disclosure relates to a photoacoustic gas sensor for detecting the presence or absence of gas using the interaction of a laser beam and gas molecules. The integrated photoacoustic gas sensor according to an embodiment includes a light output unit; a lens unit configured to concentrate a laser beam output from the light output unit; and a photoacoustic sensing unit having a quartz tuning fork aligned on the lens unit and configured to convert a vibration, generated when the laser beam passing through the lens unit interacts with gas molecules, into an electric signal.

11 Claims, 8 Drawing Sheets

(56) References Cited

U.S. PATENT DOCUMENTS

| | | | |
|---|---|---|---|
| 2012/0260719 A1 | 10/2012 | Schade | |
| 2018/0196012 A1* | 7/2018 | Blanchard | G01N 29/022 |
| 2018/0226596 A1* | 8/2018 | Moriwaki | H01L 51/5253 |
| 2018/0299369 A1* | 10/2018 | Marta | G01N 29/4436 |
| 2018/0366904 A1* | 12/2018 | Brueck | H01S 5/042 |
| 2020/0041462 A1* | 2/2020 | Levy | H03B 5/326 |
| 2020/0232906 A1 | 7/2020 | Dong et al. | |

FOREIGN PATENT DOCUMENTS

| | | |
|---|---|---|
| JP | 5060469 B2 | 10/2012 |
| JP | 5657340 B2 | 1/2015 |
| JP | 2019-529932 A | 10/2019 |
| KR | 10-2009-0010895 A | 1/2009 |

OTHER PUBLICATIONS

C Bauer et al., "A Mid-infrared QEPAS sensor device for TATP detection," Journal of Physics: Conference Series, 2009, 6 pages, vol. 157, No. 012002, IOP Publishing Ltd.

* cited by examiner

INTEGRATED PHOTOACOUSTIC GAS SENSOR AND METHOD FOR MANUFACTURING THE SAME

CROSS-REFERENCE TO RELATED APPLICATION

This application claims priority to Korean Patent Application No. 10-2020-0135896, filed on Oct. 20, 2020, and all the benefits accruing therefrom under 35 U.S.C. § 119, the contents of which in its entirety are herein incorporated by reference.

BACKGROUND

1. Field

The present disclosure relates to a photoacoustic gas sensor for detecting the presence or absence of gas using the interaction of a laser beam and gas molecules, and more specifically, to an integrated photoacoustic gas sensor in which components are vertically aligned and integrated in a single semiconductor chip, and a method for manufacturing the same.

2. Description of the Related Art

The gas detection technology is a technology that detects the presence or absence of specific gas molecules existing indoors and outdoors, and is used in various fields such as environment, safety, and national defense. Most gas sensors occupying the market are electrochemical sensors and semiconductor (MOS)-based sensors. Although the selectivity of gas types is somewhat low, they are widely used due to their small volume and low operating power.

A photoacoustic gas sensor selectively detects gas molecules by amplifying and detecting the vibration caused by the interaction between a laser beam and specific gas molecules. Despite its high selectivity and sensitivity, its market share is low due to its large volume and high price.

The quartz-enhanced photoacoustic absorption spectroscopy (QEPAS) is a technology that detects the presence or absence of gas based on the intrinsic absorption spectrum caused by the vibrational motion of gas molecules. If a laser beam passes through a quartz tuning fork (QTF) with a piezoelectric effect at regular intervals, gas molecules absorb the laser beam and generate a wave of thermal energy, which is converted into an electric signal to detect gas. In this case, if a QTF having a high Q value is used, the sensitivity of gas detection may also be increased.

The conventional QEPAS sensor occupies a relatively large volume because a large number of optical components such as lenses and mirrors for concentrating or reflecting a laser beam must be used, and there is also the inconvenience of precisely aligning components from time to time.

SUMMARY

The present disclosure is designed to overcome the drawbacks of the existing photoacoustic gas sensor (the QEPAS sensor, etc.), and the present disclosure is directed to providing an integrated photoacoustic gas sensor in which components are vertically aligned on a single semiconductor chip, and a method for manufacturing the same.

An integrated photoacoustic gas sensor according to an embodiment of the present disclosure comprises a light output unit; a lens unit disposed on the light output unit and configured to concentrate a laser beam output from the light output unit; and a photoacoustic sensing unit disposed on the light output unit and configured to convert a vibration, generated when the laser beam passing through the lens unit interacts with gas molecules, into an electric signal.

According to an embodiment, the light output unit, the lens unit and the photoacoustic sensing unit may be aligned vertically and integrated in a single semiconductor chip.

According to an embodiment, the single semiconductor chip may have a surface area of several $cm^2$ or less.

According to an embodiment, the light output unit may include a substrate; a laser active layer formed on the substrate; and a cladding layer formed on the laser active layer.

According to an embodiment, the light output unit may further include a reflection unit configured to adjust a travel direction of a laser beam emitted from the laser active layer to a vertical upward direction.

According to an embodiment, the photoacoustic sensing unit may include a U-shaped quartz tuning fork aligned on the lens unit and having an opening, gas molecules existing around the quartz tuning fork may absorb the laser beam passing through the opening to generate a photoacoustic wave, and the photoacoustic sensing unit may be configured to convert a vibration by the photoacoustic wave into an electric signal by using a piezoelectric element.

According to an embodiment, the photoacoustic sensing unit may further include an acoustic resonator configured to amplitude the photoacoustic wave.

According to an embodiment, the light output unit may include a vertical cavity surface emitting laser.

An integrated photoacoustic gas sensor according to another embodiment comprises a lens unit configured to concentrate a laser beam output from an external light source; and a photoacoustic sensing unit having a quartz tuning fork aligned on the lens unit and configured to convert a vibration, generated when the laser beam passing through the lens unit interacts with gas molecules, into an electric signal.

A method for manufacturing an integrated photoacoustic gas sensor according to an embodiment comprises forming a light output unit in which a substrate, a laser active layer and a cladding layer are stacked; etching a portion of the light output unit and forming a reflection unit on the etched portion to reflect a laser beam; disposing the light output unit on a semiconductor chip; disposing a lens unit on the light output unit to concentrate the laser beam; and disposing a photoacoustic sensing unit having a quartz tuning fork aligned with the lens unit on the light output unit.

According to an embodiment of the present disclosure, an integrated photoacoustic gas sensor in which components are vertically aligned on a single semiconductor chip is provided.

In general, in the conventional photoacoustic gas sensor, a number of optical components (a light source, a lens, a QTF, etc.) are essentially included and they are arranged horizontally on the substrate, so the size of the finished sensor occupies several ten cm or more. In addition, it is necessary to rearrange the components from time to time for operation.

Meanwhile, according to an embodiment of the present disclosure, since components are vertically aligned on a single semiconductor chip, a sensor with a much smaller volume may be manufactured. In addition, in the manufacturing stage of the sensor, once the components are aligned, realignment is not required, and the number of components may be drastically reduced, thereby significantly reducing the product cost.

DETAILED DESCRIPTION

The terms used in this specification are selected as currently widely used general terms as possible while considering their functions, but may vary depending on the intention or custom of a person skilled in the art or the emergence of new technology. In addition, in a specific case, there is a term arbitrarily selected by the applicant, and in this case, its meaning will be described in this specification. Therefore, it should be understood that the terms used in this specification should be interpreted based on the actual meaning of the terms and the contents of the entire specification, rather than simple names of the terms.

Hereinafter, embodiments will be described in detail with reference to the accompanying drawings and the contents described in the accompanying drawings, but the scope of the claims is not limited or defined by the embodiments.

Figure 1:
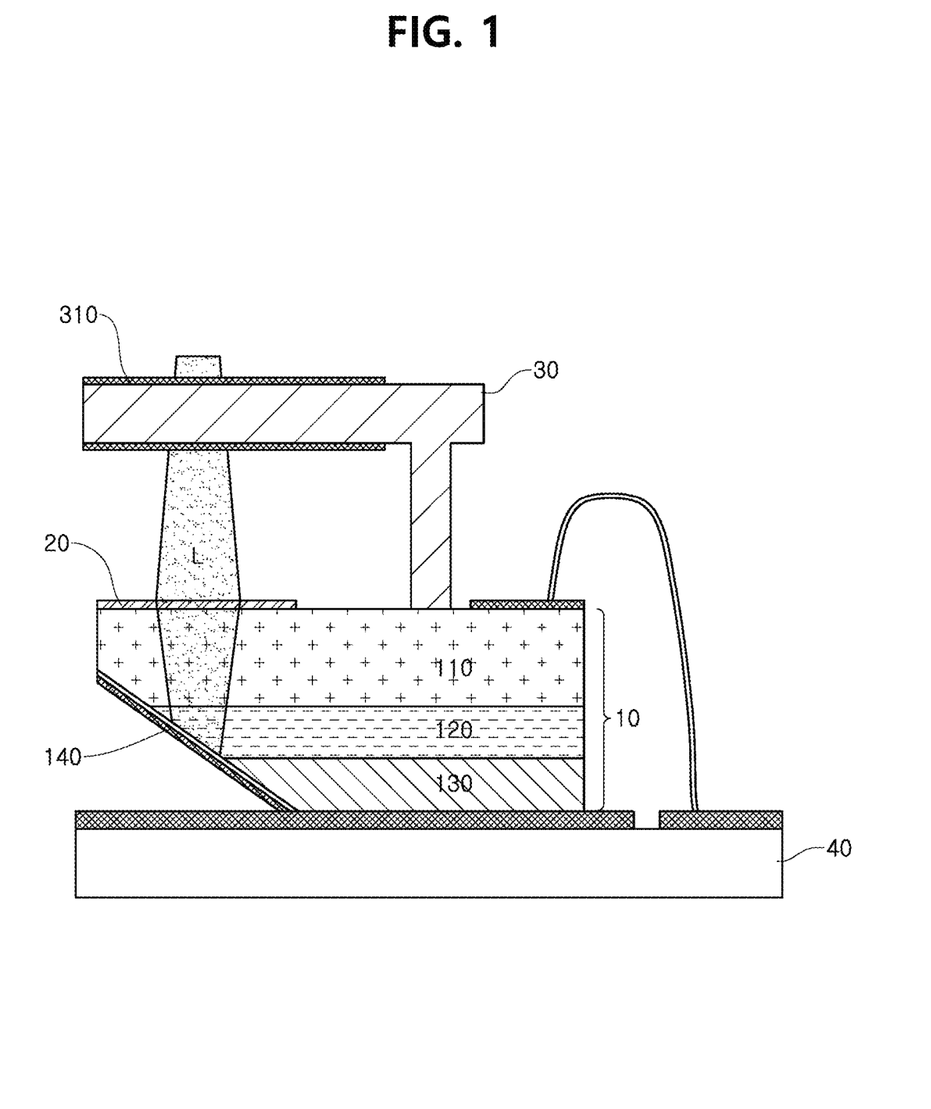
FIG. 1 is a sectional view showing a structure of a photoacoustic gas sensor according to an embodiment.

FIG. 1 is a sectional view showing a structure of a photoacoustic gas sensor according to an embodiment.

Referring to FIG. 1, the photoacoustic gas sensor according to an embodiment includes a light output unit 10, a lens unit 20 disposed on the light output unit 10, and a photoacoustic sensing unit 30 disposed on the light output unit 10. The components of the photoacoustic gas sensor are vertically disposed on a single semiconductor chip 40.

The light output unit 10 is a component for outputting a laser light irradiated toward the photoacoustic sensing unit 30 through the lens unit 20. According to an embodiment, the light output unit 10 includes a stacked structure composed of a substrate 110, a laser active layer 120 and a cladding layer 130, and a reflection unit 140 attached to an etched side of the structure.

For example, if the principle of a general semiconductor laser is used, when a current flows through a semiconductor, which is a gain medium, a pumping action occurs, and electrons and holes meet to generate light while returning to a stable state. The material or structure of the semiconductor laser changes according to the wavelength at which the absorption spectrum of a gas molecule to be detected exists. Wavelength bands of ultraviolet (UV), visible (VIS), and infrared (IR) may be used, and accordingly, semiconductor laser diodes or quantum cascade lasers may be used.

The light generated in this way travels along a waveguide in the laser active layer 120 and arrives at the reflection unit 140 attached to the edge surface of the pre-etched structure. The edge surface to which the reflection unit 140 is attached has an appropriate inclination (e.g., 45°) to change a travel path of the light, and the laser beam reflected by the reflection unit 140 travels vertically upward (i.e., a direction perpendicular to the surface of the substrate).

The lens unit 20 is disposed on a portion of the light output unit 10 to be aligned with a laser beam output terminal, and includes, for example, a convex lens or a planar lens capable of refracting the laser beam output from the light output unit 10 so that the laser beam travels straight without spreading. As the beam is concentrated more on a quartz tuning fork, explained later, it is possible to detect gas molecules with higher sensitivity.

Figure 2:
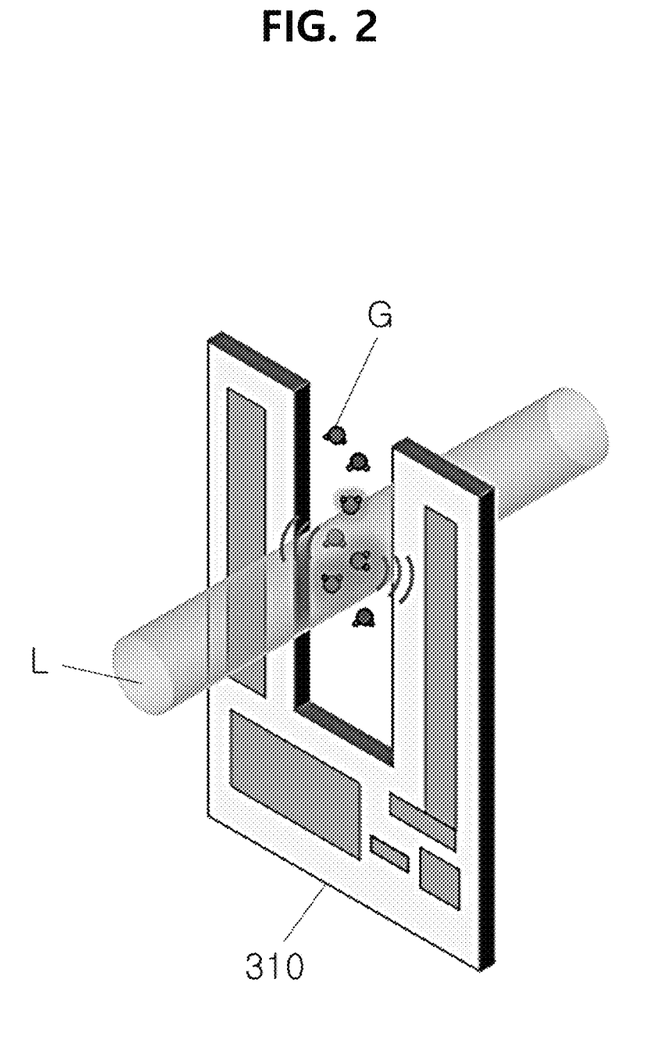
FIG. 2 shows that a laser beam passing through a quartz tuning fork (QTF) interacts with gas molecules in the photoacoustic gas sensor according to an embodiment.

The photoacoustic sensing unit 30 is disposed on the light output unit 10 and is a component for converting the vibration, generated when the laser beam passing through the lens unit 20 interacts with gas molecules, into an electric signal. The photoacoustic sensing unit 30 includes a quartz tuning fork 310 aligned on the lens unit 20, The quartz tuning fork 310 may be, for example, a U-shape (a form having an opening at one side) commonly used in a photoacoustic sensor as shown in FIG. 2. The quartz tuning fork has a high Q value, and as the Q value increases, the amount of change in electric energy according to the concentration of gas molecules increases, thereby securing higher sensitivity. The quartz tuning fork may be, for example, several millimeters in size similar to the size of a laser/photonic circuit chip, and since the laser beam is aligned according to a concentrated position, the sensor unit may be integrated on one chip.

FIG. 2 shows that a laser beam passing through a quartz tuning fork (QTF") interacts with gas molecules in the photoacoustic gas sensor according to an embodiment. As shown in FIG. 2, a laser beam L output from the light output unit 10 and concentrated by the lens unit 20 passes through an opening (a perforated portion) of the quartz tuning fork 310. At this time, a gas molecule G absorbs the laser beam L to generate a photoacoustic wave, and the photoacoustic sensing unit converts the vibration caused by the photoacoustic wave into an electric signal by using a piezoelectric element. A processor connected to the gas sensor processes the electric signal to obtain related information such as type and density of the gas.

According to an embodiment, the photoacoustic sensing unit 30 may further include an acoustic resonator that amplifies the photoacoustic wave.

Figure 3:
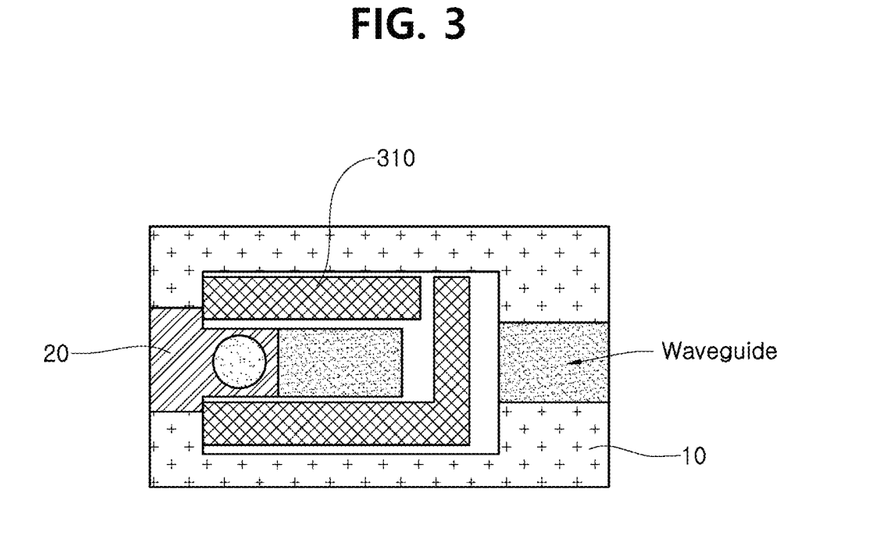
FIG. 3 is a plan view showing the photoacoustic gas sensor according to an embodiment.

FIG. 3 is a plan view showing the photoacoustic gas sensor according to an embodiment.

As described above, the laser light generated by the light output unit 10 travels along a waveguide and is reflected by the reflection unit to be output in a vertical upward direction. The output laser beam is concentrated by the lens unit 20 and passes through the quartz tuning fork 310 to detect the presence or absence of gas by processing the electric signal generated by the piezoelectric effect.

According to this structure, since components such as the light output unit, the lens unit and the photoacoustic sensing unit are vertically aligned on a single semiconductor chip, the components occupy a much smaller volume, compared to a conventional structure in which components are horizontally arranged on a semiconductor chip. Preferably, since the surface area of the semiconductor chip on which the integrated gas sensor is aligned according to the embodiment is several $cm^2$ or less, it is possible to provide a gas sensor that is portable and highly useful.

In addition, unlike the existing QEPAS structure using a large number of optical components that must be aligned from time to time, in the present disclosure, realignment is not required once the components are aligned in the manufacturing stage, and the number of components may also be drastically reduced, thereby greatly reducing the product cost.

Hereinafter, a structure of a photoacoustic gas sensor according to another embodiment, different from the structure according to the former embodiment, will be described.

Figure 4A:
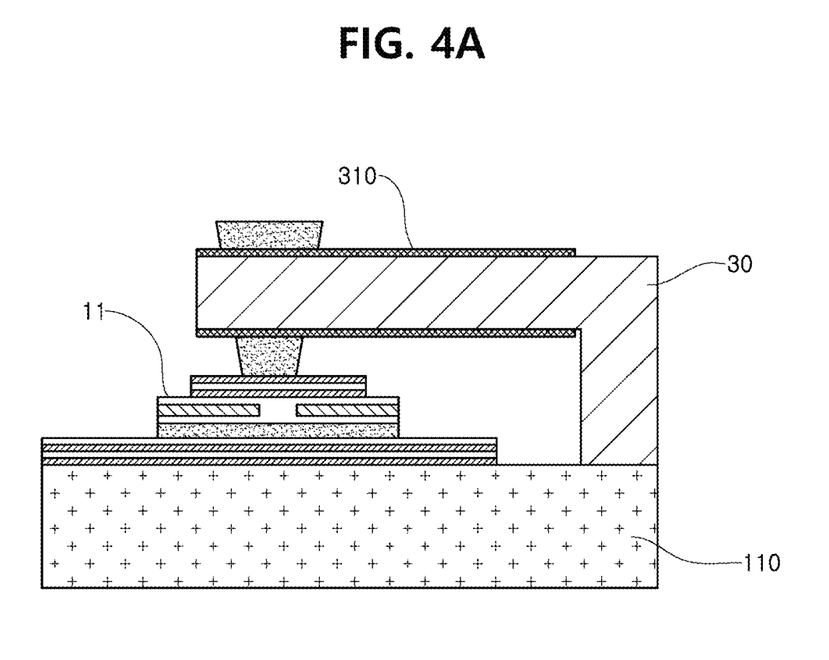
FIGS. 4A and 4B are a sectional view and a plan view showing a photoacoustic gas sensor according to another embodiment.
Figure 4B:
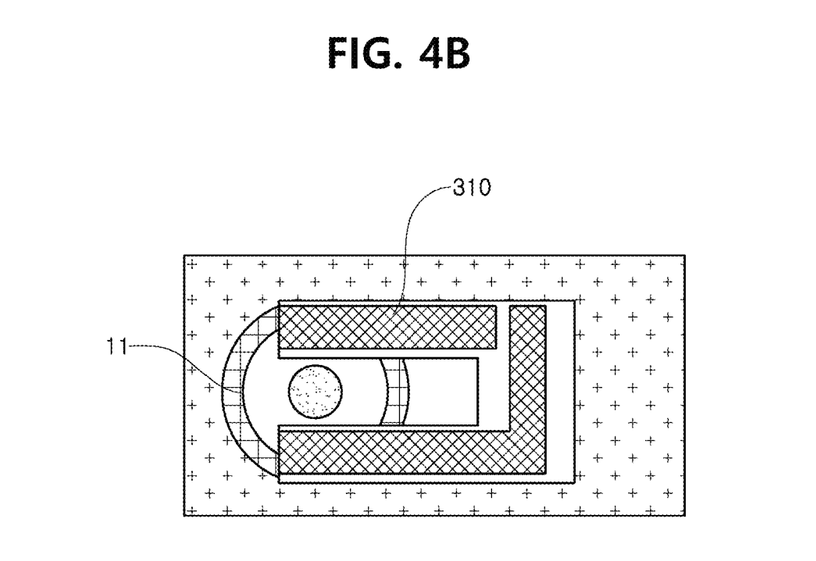

FIGS. 4A and 4B are a sectional view and a plan view showing a photoacoustic gas sensor according to another embodiment. The structure shown in FIGS. 4A and 4B uses a vertical cavity surface emitting laser device instead of the stack-type semiconductor laser device and the mirror reflection unit described above. That is, the light output unit 11 does not require a separate structure such as a reflection mirror, a waveguide and a condensing lens because it outputs a laser in a vertical upward direction according to power supply. The other structures detect the presence or absence of gas based on the interaction between the laser beam and gas molecules existing in the opening of the quartz tuning fork 310 by the photoacoustic sensing unit 30 disposed on the substrate 110, similar to in the former embodiment.

According to still another embodiment of the present disclosure, the integrated photoacoustic gas sensor may include only a lens unit and a photoacoustic sensing unit except for the light output unit. In this case, gas is detected using a laser beam output from an external light source. According to the structure that does not include the light output unit as described above, the overall size of the system including the external light source may be increased, but there is an advantage that several types of gas molecules may be detected using one sensor.

Hereinafter, a method for manufacturing a photoacoustic gas sensor will be described with reference to the drawings.

FIGS. 5A to 5F are sectional views of each step for illustrating a method for manufacturing the photoacoustic gas sensor according to an embodiment.

Figure 5A:
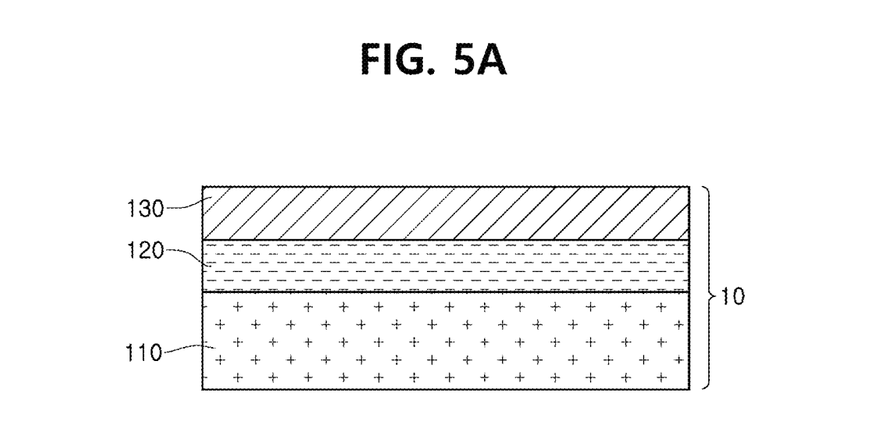
FIGS. 5A to 5F are sectional views of each step for illustrating a method for manufacturing the photoacoustic gas sensor according to an embodiment.

Referring to FIG. 5A, a light output unit 10 in which a first the substrate 110, a laser active layer 120 and a cladding layer 130 are stacked is formed. The substrate 110 may be made of, for example, silicon, glass, III-V compound semiconductors, or a combination thereof, but is not limited thereto. The laser active layer 120 is a layer that generates light when an electric current is supplied, and includes a waveguide core that is a path through which light travels.

Figure 5B:
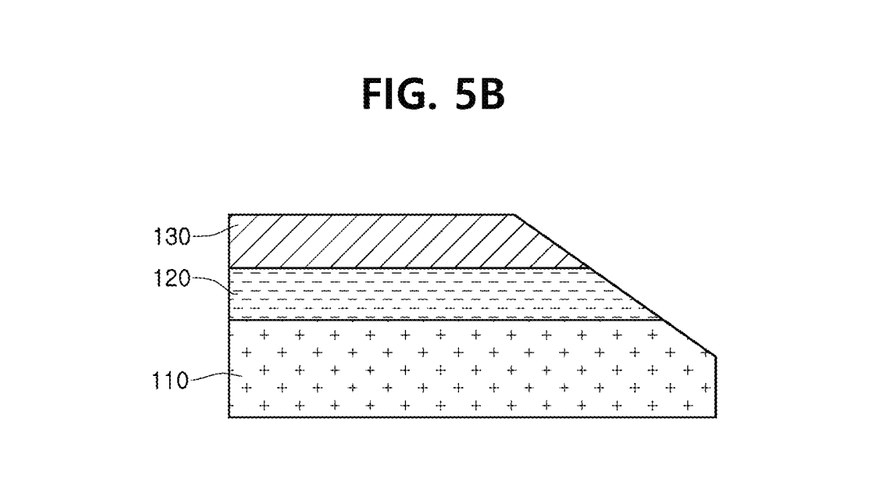

Subsequently, a portion of the light output unit 10 is etched as shown in FIG. 5B. The inclination of the etched surface is preferably 45°, but may vary depending on the location or arrangement of the components.

Figure 5C:
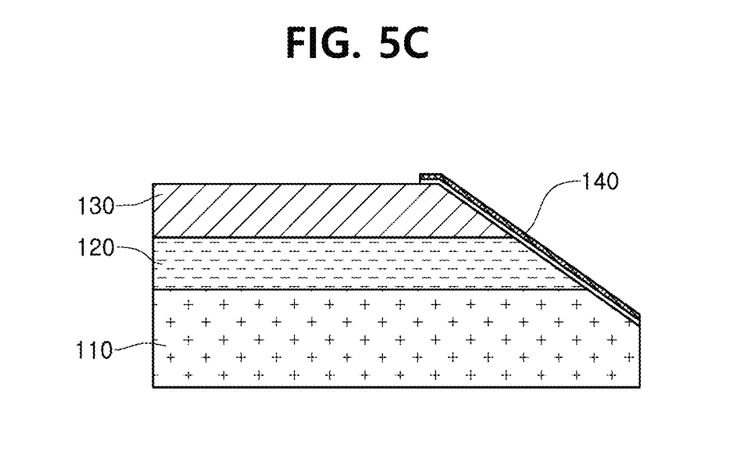

Subsequently, as shown in FIG. 5O, a reflection unit 140 for reflecting a laser beam is formed on the etched portion. The reflection unit 140 may adjust the travel direction of the laser beam traveling along the waveguide of the laser active layer into a direction perpendicular to the substrate.

Figure 5D:
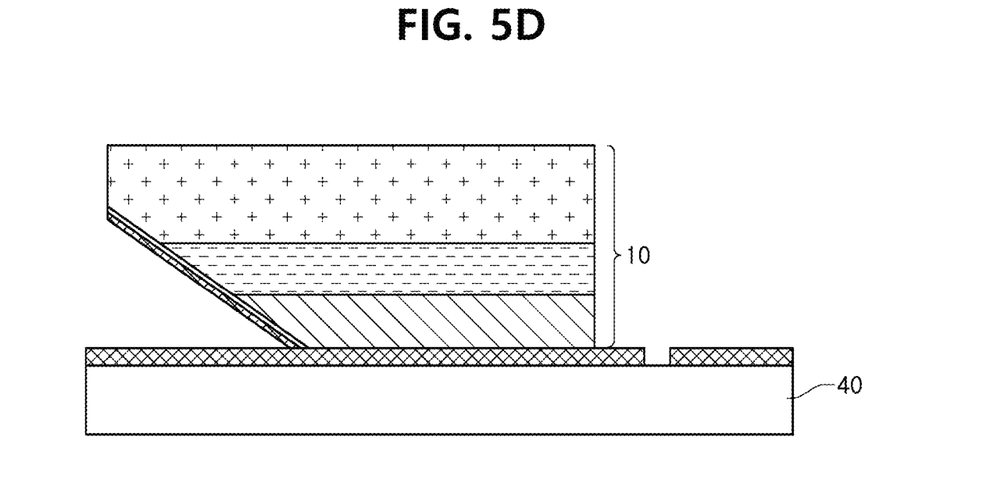

Subsequently, as shown in FIG. 5D, the light output unit 10 to which the reflection surface is attached is turned over and disposed on the semiconductor chip 40. Since the surface area of the semiconductor chip 40 is preferably several cm² or less as described above, it is possible to manufacture an integrated gas sensor having a much smaller volume than that of a conventional structure.

Figure 5E:
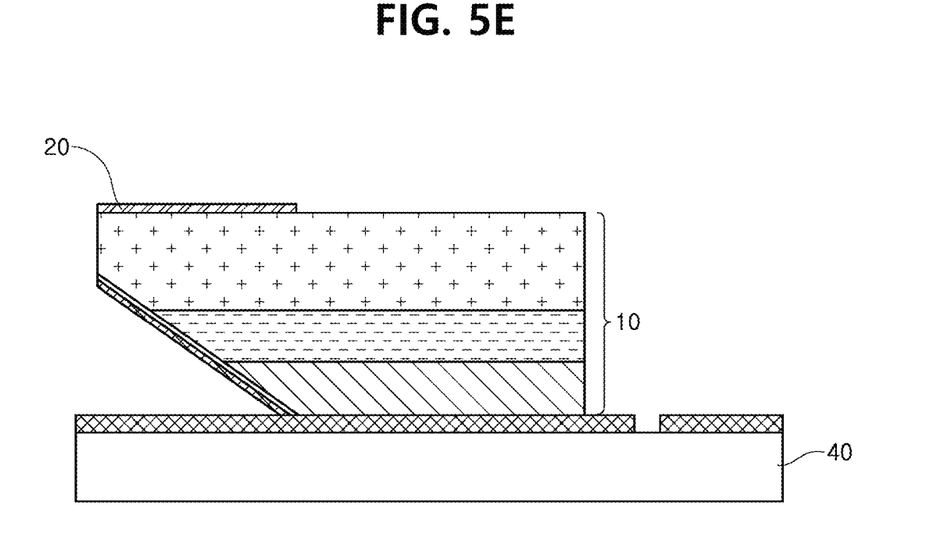

Subsequently, the lens unit 20 is placed on the inverted light output unit 10 as shown in FIG. 5E. The lens unit 20 is arranged to align with the laser beam output terminal, and helps the laser beam to travel straight without spreading.

Figure 5F:
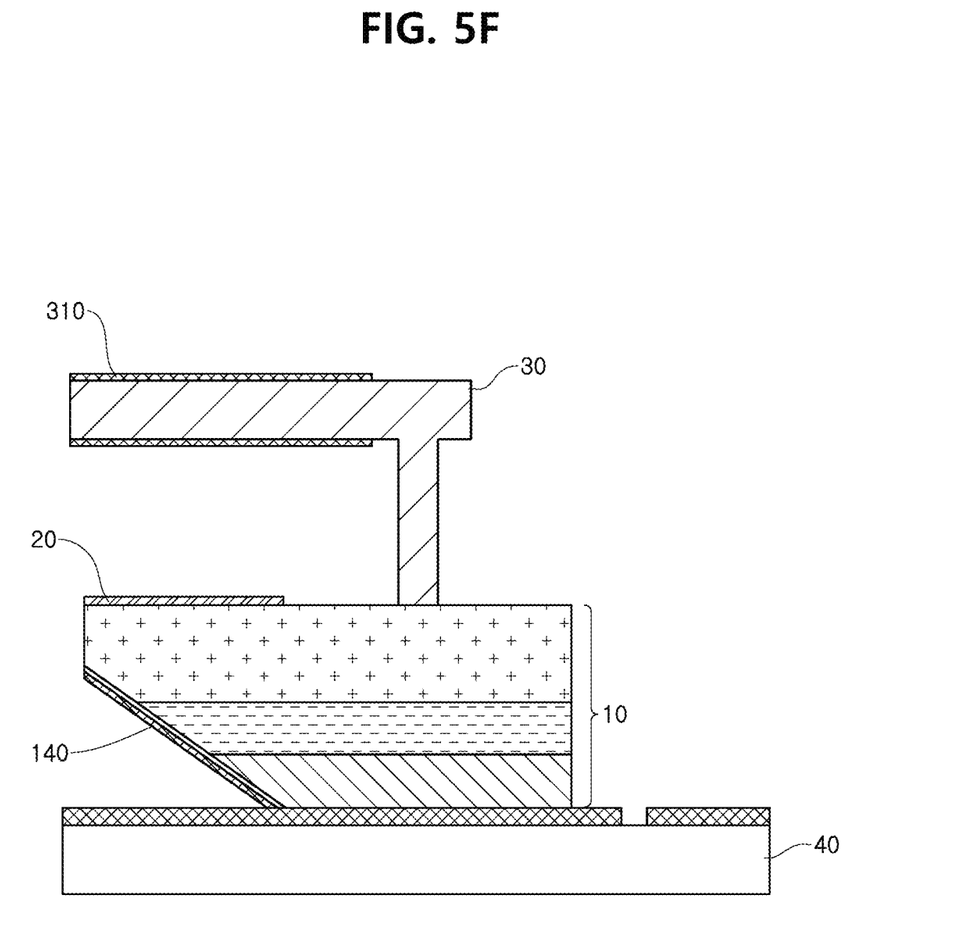

Finally, the photoacoustic sensing unit 30 is disposed on the light output unit 10 as shown in FIG. 5F. The photoacoustic sensing unit 30 has a U-shaped quartz tuning fork 310 aligned on the lens unit 20. According to an embodiment, the quartz tuning fork 310 may have a U-shape having an opening used in a general photoacoustic sensor. The quartz tuning fork may be, for example, several millimeters in size similar to the size of a laser/photonic circuit chip, and since the laser beam is aligned according to a concentrated position, the sensor unit may be integrated on one chip.

As described above, the light output unit 10, the lens unit 20 and the photoacoustic sensing unit 30 are vertically aligned and integrated on a single semiconductor chip 40. According to this structure, the components occupy a much smaller volume compared to the conventional QEPAS structure in which components are individually disposed on a semiconductor chip. In addition, the existing QEPAS uses a large number of optical components and has a disadvantage that components must be aligned from time to time, but according to the structure of this embodiment, realignment is not required after the components are once aligned ire the manufacturing stage, and the number of components may also be significantly reduced, thereby greatly reducing the product cost.

Although the present disclosure has been described above with reference to the embodiments, it should be understood that the present disclosure can be changed and modified by those skilled in the art in various ways without departing from the idea and scope of the present disclosure defined in the appended claims.

What is claimed is:

1. An integrated photoacoustic gas sensor, comprising:
   a light output unit;
   a lens unit disposed on the light output unit and configured to concentrate a laser beam output from the light output unit; and
   a photoacoustic sensing unit disposed on the light output unit and configured to convert a vibration, generated when the laser beam passing through the lens unit interacts with gas molecules, into an electric signal;
   wherein the lens unit and the photoacoustic sensing unit are aligned vertically and integrated in a single semiconductor chip.

2. The integrated photoacoustic gas sensor according to claim 1, wherein the light output unit is aligned vertically with the lens unit and the photoacoustic sensing unit in the single semiconductor chip.

3. The integrated photoacoustic gas sensor according to claim 2, wherein the single semiconductor chip has a surface area of several cm² or less.

4. The integrated photoacoustic gas sensor according to claim 1,
   wherein the light output unit includes:
   a substrate;
   a laser active layer formed on the substrate; and
   a cladding layer formed on the laser active layer.

5. The integrated photoacoustic gas sensor according to claim 4,
   wherein the light output unit further includes a reflection unit configured to adjust a travel direction of a laser beam emitted from the laser active layer to a vertical upward direction.

6. The integrated photoacoustic gas sensor according to claim 1,
   wherein the photoacoustic sensing unit includes a U-shaped quartz tuning fork aligned on the lens unit and having an opening,
   wherein gas molecules existing around the quartz tuning fork absorb the laser beam passing through the opening to generate a photoacoustic wave, and wherein the photoacoustic sensing unit is configured to convert a vibration by the photoacoustic wave into an electric signal by using a piezoelectric element.

7. The integrated photoacoustic gas sensor according to claim 6,
wherein the photoacoustic sensing unit further includes an acoustic resonator configured to amplify the photoacoustic wave.

8. The integrated photoacoustic gas sensor according to claim 1,
wherein the light output unit includes a vertical cavity surface emitting laser.

9. An integrated photoacoustic gas sensor, comprising:
a lens unit configured to concentrate a laser beam output from an external light source; and
a photoacoustic sensing unit having a quartz tuning fork aligned on the lens unit and configured to convert a vibration, generated when the laser beam passing through the lens unit interacts with gas molecules, into an electric signal;
wherein the lens unit and the photoacoustic sensing unit are aligned vertically and integrated in a single semiconductor chip.

10. The integrated photoacoustic gas sensor according to claim 9, wherein the single semiconductor chip has a surface area of several $cm^2$ or less.

11. The integrated photoacoustic gas sensor according to claim 9,
wherein the photoacoustic sensing unit comprises a U-shaped quartz tuning fork aligned on the lens unit and having an opening,
wherein gas molecules existing around the quartz tuning fork absorb the laser beam passing through the opening to generate a photoacoustic wave, and
wherein the photoacoustic sensing unit is configured to convert the vibration by the photoacoustic wave into the electric signal by using a piezoelectric element.

* * * * *